(12) United States Patent
Sprenger

(10) Patent No.: US 8,100,691 B2
(45) Date of Patent: Jan. 24, 2012

(54) BAR MATRIX

(75) Inventor: Peter Sprenger, Hilzingen (DE)

(73) Assignee: Peter Sprenger Dental Technik, Zürich (CH)

( * ) Notice: Subject to any disclaimer, the term of this patent is extended or adjusted under 35 U.S.C. 154(b) by 194 days.

(21) Appl. No.: 12/311,150

(22) PCT Filed: Jul. 6, 2007

(86) PCT No.: PCT/CH2007/000329
§ 371 (c)(1),
(2), (4) Date: Mar. 19, 2009

(87) PCT Pub. No.: WO2008/034267
PCT Pub. Date: Mar. 27, 2008

(65) Prior Publication Data
US 2009/0269715 A1   Oct. 29, 2009

(30) Foreign Application Priority Data

Sep. 21, 2006   (CH) ..................................... 1507/06
Apr. 4, 2007   (CH) ..................................... 0540/07

(51) Int. Cl.
*A61C 13/12* (2006.01)
*A61C 13/00* (2006.01)

(52) U.S. Cl. .................. 433/172; 433/167; 433/177

(58) Field of Classification Search .................. 433/167, 433/169–177, 181–183, 199.1
See application file for complete search history.

(56) References Cited

U.S. PATENT DOCUMENTS

| 1,367,885 | A | * | 2/1921 | Means ........................ 433/169 |
| 4,209,904 | A | | 7/1980 | Staubli |
| 5,427,906 | A | * | 6/1995 | Hansen ........................ 433/173 |
| 2003/0211444 | A1 | | 11/2003 | Andrews |

FOREIGN PATENT DOCUMENTS

| DE | 30 09 758 A1 | 9/1981 |
| DE | 38 39 112 A1 | 6/1989 |
| DE | 296 09 304 U1 | 9/1996 |
| DE | 20 2005 006 941 U1 | 9/2006 |
| EP | 1 192 916 A2 | 4/2002 |

* cited by examiner

*Primary Examiner* — John J Wilson
(74) *Attorney, Agent, or Firm* — Pauley Petersen & Erickson

(57) ABSTRACT

For a resilient mounting of a spider die onto a dental prosthetic suprastructure on a male spider mold, at least one retention element is molded onto a sleeve, and the retention element has a substantially occlusal alignment. The at least one retention element extends across the entire length of the sleeve and has a head having a connecting neck in its cross-section. In this manner, retention undercuts are formed on both sides of the connecting neck. The connecting neck of the at least one retention element is molded at an offset as opposed to the crown line of the sleeve. A spider die is thus created, which has an improved retention with an increased retention force at a smaller installation height.

12 Claims, 4 Drawing Sheets

BAR MATRIX

BACKGROUND OF THE INVENTION

1. Field of the Invention

This invention relates to a bar matrix for the fastening of a dental prosthetic supra-construction on a bar projection.

2. Discussion of Related Art

Bar matrices are part of a bar attachment, with which part prosthesis or total prosthesis are held in the lower jaw or upper jaw, in an implant-retained manner. Such bar attachments have a bar projection and a bar matrix. The bar projection is a fine-mechanical anchoring element, which includes a crosspiece which runs between implants and orally blocks these with one another. The complete crosspiece with the fastener for fastening on the implants is called a bar projection.

A bar matrix is integrated into the removable part of the tooth prosthesis. The bar matrix, often also called bar rider, has a sleeve with suitable retention elements, in order to effect an anchoring in the dental-prosthetic supra-construction.

With modern supra-constructions, a metallic support construction should be present, on which the actual supra-construction of plastic is held. The support construction is called the cast model. The cast model includes openings for connecting the cast model to the plastic construction, which are indicated as so-called polymerization windows.

While the development, which is often made by dentists, has concerned itself primarily with the releasable connection between the bar matrix and the bar projection, the problem of the anchoring of the bar matrix in the dental-prosthetic supra-construction has been neglected, because this problem essentially occurs only in dental laboratories, which concern the manufacture of the dental-prosthetic supra-construction. Indeed, on manufacture of the dental-prosthetic supra-construction, it has been found that the retention elements are capable of accommodating only an insufficient retention force on the sleeve of the bar matrix, because the retention elements could only be kept extremely small on account of the design. The constructions of the bar matrices common today envisage a sleeve which is at least approximately u-shaped in cross section and which practically along the apex line in each case has a longitudinal surface running buccally and lingually, the longitudinal surfaces having a maximal extension in the lingual and buccal direction, so that they do not exceed the sleeve width. This is necessary, because otherwise the wall thickness of the dental-prosthetic supra-construction or of the tooth construction would be too thin-walled or would project outward.

The bar attachment is a development by Dr. Hans Dolder that represents a solution for holding dental prosthesis which are supported not only in a purely gingival manner. As mentioned, this Dolder bar has been proven over many years. A further development of this Dolder bar is shown for example in European Patent Reference EP 1 192 916, with which the fastening of the matrix onto the projection functioning as a bar, does not function with a resilient mechanical retention, but with a permanent magnet in a shape to the bar, and is surrounded by a sleeve. With this solution, the retention elements are integrally formed in a lingual and buccal manner and form the shape of an elongate, laterally integrally formed lug. Here, the anchoring of the dental-prosthetic supra-construction is only rudimentarily realized.

A bar matrix is known from German Patent Reference DE-3009758A, which is a sleeve with pins which are integrally formed thereon and running in the occlusal direction. The retention forces which may be achieved with these are minimal.

In contrast, the conventional solution according to German Patent Reference DE-29609304 U, with which the bar matrix is formed as a sleeve with wings which are integrally formed in a buccal and lingual manner.

A bar projection which is practically integrally formed on the patient, and with which accordingly also the bar matrix which is formed as a U-shaped sleeve rectangular in cross section, and the matrix and projection are molded to one another, is completely unusual. The solution according to U.S. Patent Application Publication US-2003/0211 444 may thus not be combined with a Dolder bar.

Finally, a bar matrix is known from U.S. Pat. No. 4,209,904, which is formed from a number of riders which may be placed on the Dolder bar, wherein the riders have a sleeve section, on which a tab bent in the occlusal direction is integrally formed. The solution is only suitable for supra-constructions without a cast model, thus without metal reinforcement. If the tabs are located at a location where the pallatinal surface of the teeth runs very close to the bar, then the retention tabs must be ground away, and the retention is greatly weakened.

SUMMARY OF THE INVENTION

It is one object of this invention to provide a bar matrix of the initially mentioned type, but so that the retention forces from the bar matrix to the dental-prosthetic supra-construction may be increased, without at the same time weakening the dental-prosthetic supra-construction attached thereon, or having to accept other disadvantages of the state of the art.

A bar matrix according to this invention achieves this object. The continuous design of the retention elements permits the dental technician to adapt the retention element at any location, to the given circumstances, by grinding, without the sleeve becoming damaged, a weakening of the construction occurring or other negative effects occurring.

In most cases, significantly more space is available in the occlusal direction, for the dental laboratory technician who creates a dental-prosthetic supra-construction. Because the forces which occur on use act essentially in an occlusal manner, it is necessary for the retention elements or the at least one retention element to be undercut, deviating from the occlusal direction.

BRIEF DESCRIPTION OF THE DRAWINGS

Some embodiments of the subject matter of this invention are represented in a simplified manner in the drawing, and are explained in the subsequent description, wherein.

DETAILED DESCRIPTION OF THE INVENTION

Figure 1:
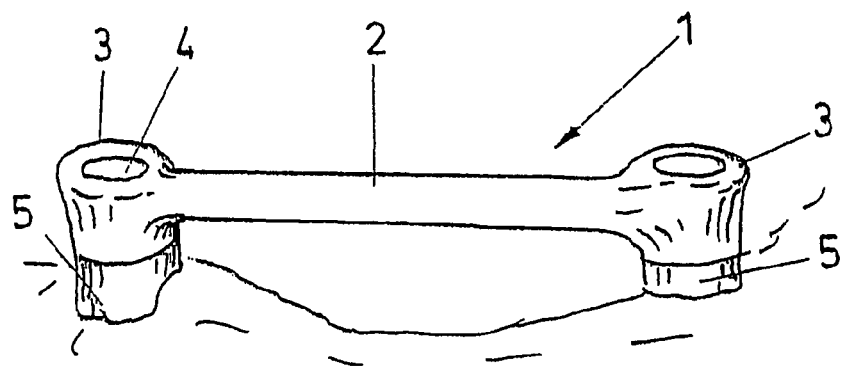
FIG. 1 is a view of a Dolder bar fastened on two implants, in a perspective view.
Figure 7:
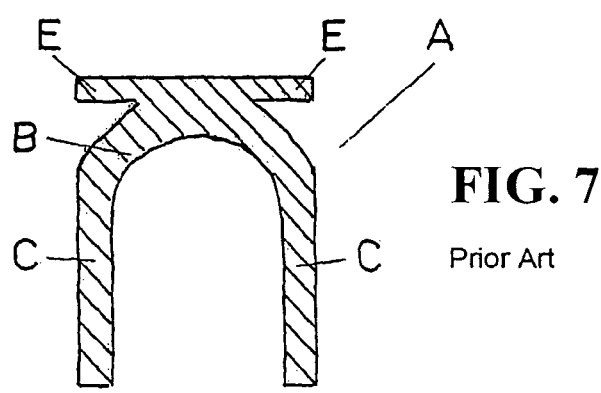
FIG. 7 shows a bar matrix of the conventional type in a reduced scale.
Figure 4:
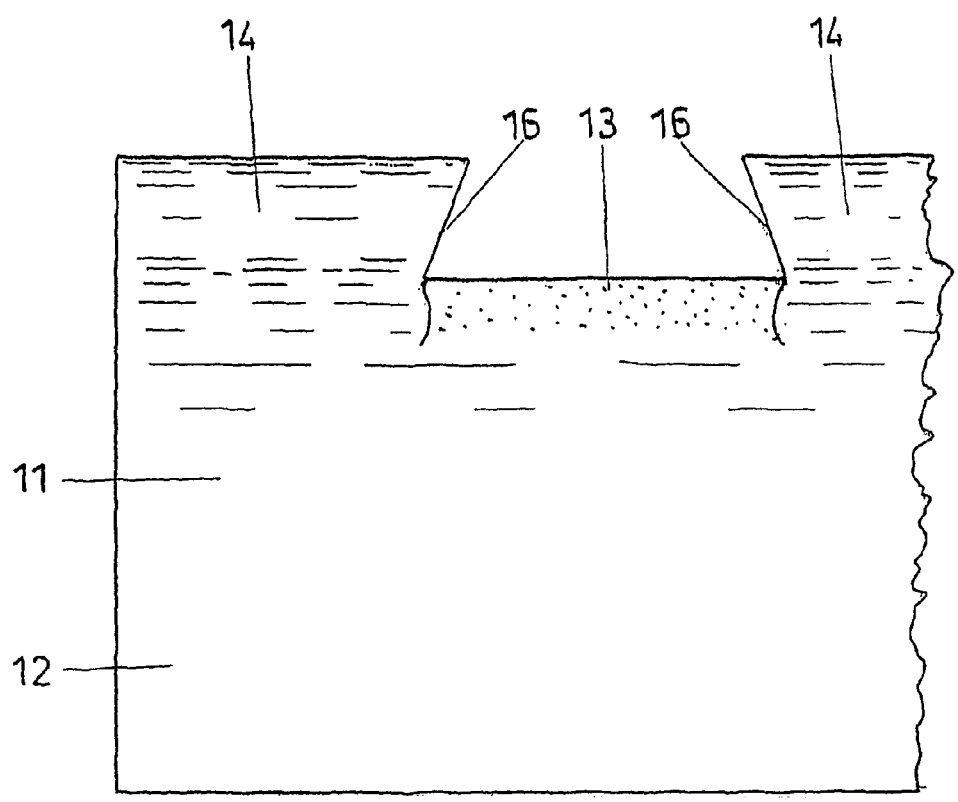
FIG. 4 shows a partial view of a bar matrix from a side.

FIG. 7 shows a conventional bar matrix in cross section. The bar matrix forms the clamping part, with which a complete prosthesis or part prosthesis is resiliently held on a bar projection. In the inserted condition, the part-prosthesis or complete prosthesis completely covers the Dolder bar, according to FIG. 1. The length of the bar matrix thereby corresponds maximally to the length of the crosspiece or bar 2. The actual bar matrix is indicated at A and includes an elongate sleeve B which is arch-like in cross section. This sleeve B is often also called a rider sleeve because it is placed on the crosspiece 2 of a bar projection 1. The rider sleeve B is delimited in the longitudinal direction on both sides by clamping walls C. These merge into a bearing bow. Retention elements E are integrally formed in the regions of the bearing bow. The course of retention elements runs precisely in a buccal-lingual manner. Because the forces of the dental-prosthetic supra-construction run essentially in the occlusal direction, then it is not the direction so much, but the size of the retention elements which is of significance. An enlargement of the retention elements is not possible with the previous design, because they lead beyond a width of the two clamping walls.

Figure 2:
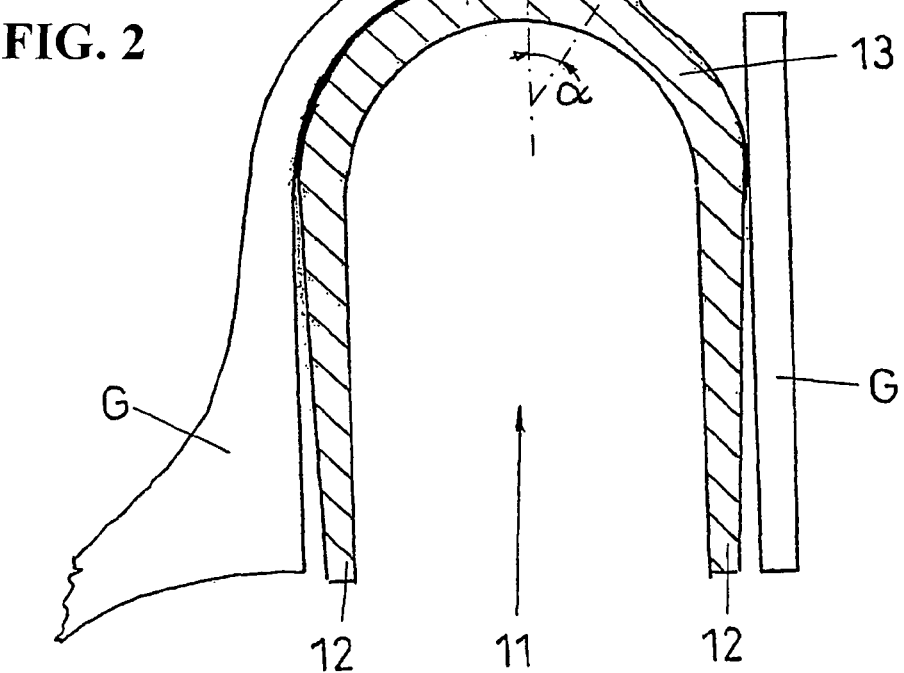
FIG. 2 shows a section taken through a first embodiment of a bar matrix, perpendicular to a longitudinal alignment.

One preferred embodiment of the matrix according to this invention is shown in a cross section taken along the alignment of the bar matrix in FIG. 2. The bar matrix as a whole is indicated as element reference numeral 10, and comprises the sleeve or the rider sleeve 11, which comprises two clamping walls 12 running longitudinally and arranged roughly in parallel. The two clamping walls 12 merge into a bearing bow 13. At least one retention element 14 which is aligned essentially in the occlusal direction is present on the bearing bow 13. Thus, the shaping of the retention element 14 is such that at least one undercut deviating from the occlusal direction rises. Because, with chewing movements, it is not only forces in the occlusal direction which occur on the dental supra-construction, but also force components differing from this direction and occurring essentially in the buccal or lingual direction, the arrangement of the at least one retention element 14 running essentially in the occlusal direction is particularly advantageous, because these force components may also be accommodated in an optimal manner.

Two retention elements are shown in the embodiment according to FIG. 2. A first retention element is practically only aligned in the occlusal direction and is indicated as element reference numeral 141. The first retention element 141 runs over the whole length of the bar matrix 10, or over the whole length of the sleeve 11. It has essentially a cross sectional shape which forms a head 143 and which is connected as one piece on a neck 144 to the bearing bow 13. Undercuts 145 which are capable of accommodating forces essentially occurring in the occlusal direction with a positive fit, arise on both sides because of the neck 144 of the first retention element 141. However, in order to better anchor the anchoring of the cast material of the dental-prosthetic supra-construction which is deposited over this, in this embodiment, a second retention element 142 is provided, which is integrally formed inclined at an angle a with respect to the first retention element 141. The second retention element in the same manner runs parallel to the longitudinal direction of the bar matrix 10, and likewise parallel to the first retention element 141. Because of this inclined shape, an even greater undercut 146 results below the second retention element 142.

The whole sleeve 11 is a premanufactured element which dental laboratories purchase and process further by incorporating the sleeve 11 into a cast model G, and the prosthesis teeth are formed thereabove. The retention elements 14 project through the cast model G, and serve for retention of the dental-prosthetic supra-construction with a positive fit. With this, a gap which permits a certain spring movement of the clamping walls 12, remains between the clamping walls 12 of the sleeve 11 and the cast model G.

The continuous design of retention elements permits the dental technician to adapt the retention element to the conditions at any location, by grinding, without the sleeve getting damaged, a weakening of the construction occurring or other negative effects occurring.

Figure 3:
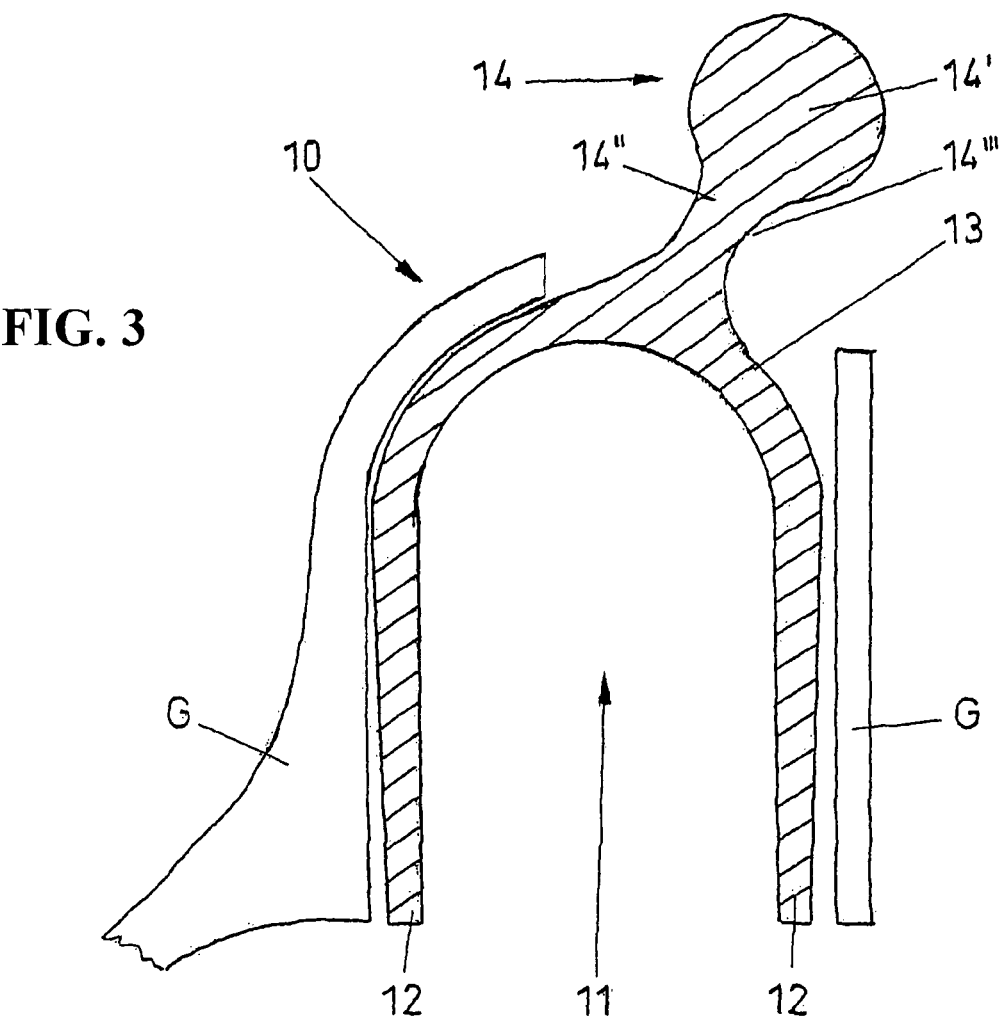
FIG. 3 shows a second embodiment of a section taken through a bar matrix, perpendicular to a longitudinal alignment.

A second preferred embodiment of the subject-matter of this invention is shown in FIG. 3 in the same representation as FIG. 2. Again the bar matrix 10 comprising the sleeve 11 is shown embedded in the cast model G, and the sleeve 11 has clamping walls 12, which run parallel to one another and whose wall thicknesses, just as with the embodiment according to FIG. 2, slightly taper conically from the bearing bow 13 towards the ends, in order to increase the spring effect of the clamping walls 12. This time, a single retention element 14 is integrally formed on the bearing bow 13. The single retention element 14 extends over the whole length of the sleeve 11 and here too has a head 14' and a neck 14". The retention element 14 is aligned essentially in the occlusal direction, but as with the previous embodiment, has an inclination in the buccal or lingual direction with respect to the second retention element 142. The inclination in the buccal or lingual direction is dependent on the installation position and is determined by the dental laboratory. Usually, the installation position is such that the retention element 14 in the installed condition tends to be directed buccally outwards. If a single retention element is present, then this may be designed larger than with the variant with which two retention elements are present running parallel to one another in the same manner. The inclination essentially serves for realizing an enlarged undercut 14'". The inclination of the retention element is usually selected between 0° and 45°, more preferably however between 10° and 30°. If two retention elements are present, as with the previously described embodiment, then of course one can have a buccal inclination and the other a lingual inclination, or also only one of the two may have an inclination. Accordingly, the angle α is variable to a large extent. However, most preferably it is not more than maximally 90° and preferably the angle α is between 10° and 45°. With the design of the solution with two retention elements running in the longitudinal direction, as shown in FIG. 2, one would make the length of the connection necks 144 and 147 differently long, to design the heads of the retention elements adequately large and simultaneously to ensure a perfect flowing-in of the mass for forming the dental-prosthetic supra-construction.

Figure 6:
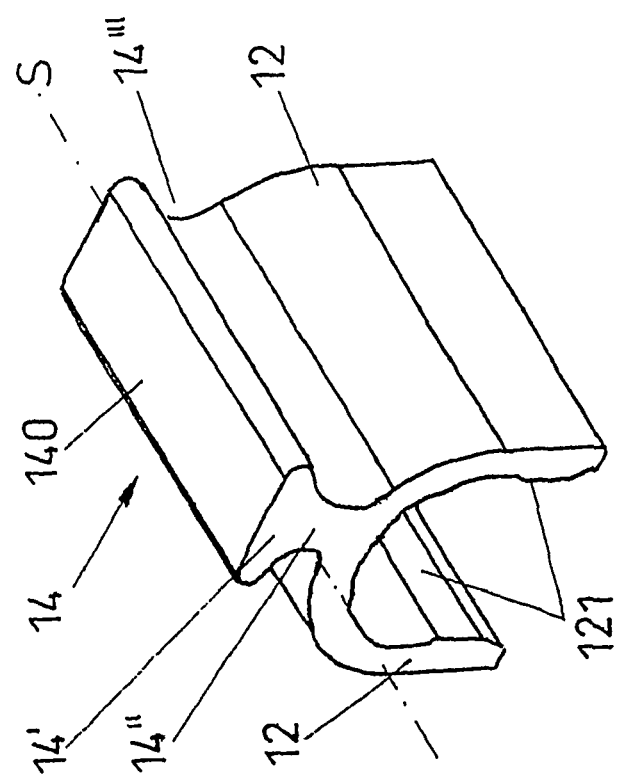
FIG. 6 is a perspective view of another embodiment.

The dental laboratory technician, with regard to the embodiment according to FIG. 2 and the embodiment according to FIG. 3, may himself take further measures, in order to increase the retention and simultaneously also to make certain shape adaptations of the sleeve. This is shown in FIG. 6, in which a sleeve 11 with the single retention element 14 is shown from a side. The retention element is thus interrupted by a suitable sawing-in, milling-away or filing, so that it has an undercut. This application, with which the undercut edges are formed running inclined in a distal and medial manner, emanates from sleeves with retention elements extending continuously over their whole length. If one manufactures the sleeve 11 in a mold casting procedure, then the undercut edges 16 on the retention element 14 may also be ideally formed directly from the beginning. Because the dental laboratory can carry out adaptations anyway in the normal case, a solution with which the dental laboratory incorporates the undercut edges is preferred.

Figure 5:
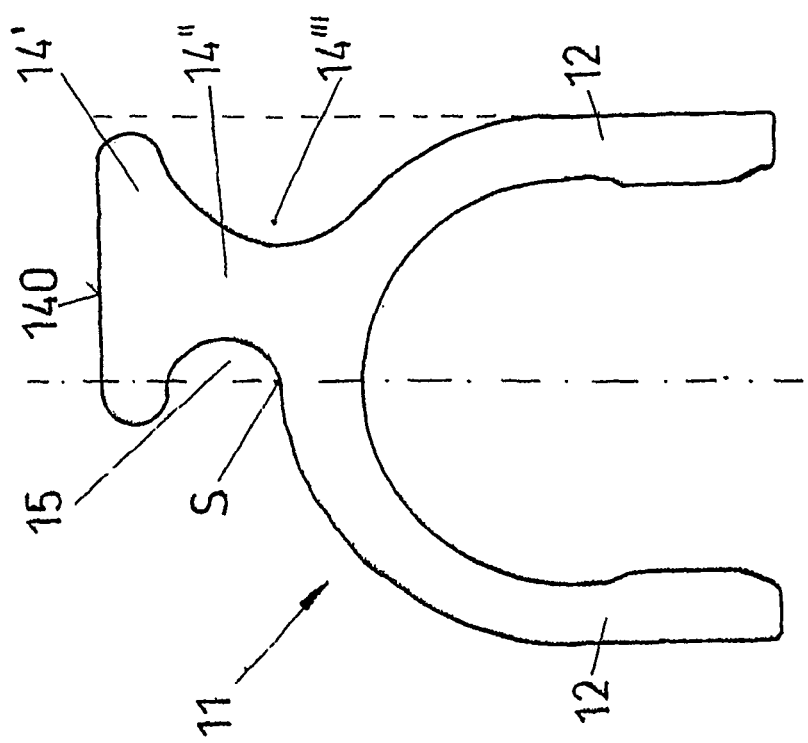
FIG. 5 shows one embodiment of a bar matrix with a differently designed cross-sectional shape, in a lateral view.

In one embodiment of the bar matrix 10 as shown in FIG. 5 and FIG. 6, a continuous extension is adapted to the length of the bar projection. The sleeve 11 comprises two clamping walls 12, which are connected to one another via the bearing bow 13. The clamping walls 12 have step-like thickenings, with the clamping strips 121 incorporated on their inner side, for increasing the retention force of the sleeve 11 out of the bar 2.

The sleeve 11 is mirror-symmetrical with respect to the longitudinal axis or with respect to the apex line S of the bearing bow. The neck 14" of the single retention element 14 is integrally formed eccentrically to the apex line S. The neck 14" represents the connection to the head 14' of the retention element 14. The head has a different cross-sectional shape compared to the examples described earlier. Basically, the cross-sectional shape of the head 14' can have any shape.

In the shape represented, the head has a widening running transversely to the longitudinal direction, which thus runs in the buccal-lingual direction. There is a flattening 140 of the head 14'. The flattening 140 is preferred, in order to avoid a notch effect below the forces in the supra-construction which occur in the occlusal direction. The flattening can run perpendicular to the occlusal direction.

The eccentric alignment of the neck 14" of the retention element 14 is associated with the different course of the pallatinal surfaces of the teeth. The eccentric arrangement of the head 14' should be such that the head does not project beyond the extension of the clamping walls on any side. The outer, buccal tooth surfaces if anything, run perpendicularly, while pallatinally, the tooth surfaces run inclined towards the buccal direction. Thus in the installation position, the retention element 14 is displaced away from the pallatinal side. Thus the pallatinal surface would be located on the left in FIG. 5.

This arrangement leads to the undercut between the sleeve and head 14' on the one side, normally the buccal side, being smaller than on the pallatinal side, where one mostly has more space.

The bar matrix according to this invention permits best space utilization with an optimal anchoring even with restricted spatial conditions, because of its special shaping which may be correctly adapted to each supra-construction.

What is claimed is:

1. A bar matrix (10) for fastening a dental-prosthetic supra-construction on a bar projection (1), wherein the bar matrix has a sleeve (11) which in cross section is bent at least approximately in a U-shape, which can be held onto the bar projection and on which at least one retention element (14) is arranged for the retention of the dental-prosthetic supra-construction, the at least one retention element (14, 14', 14"; 141; 142) is a part integrally formed on the sleeve and with an essentially occlusal alignment, the bar matrix comprising: the at least one retention element (14; 14', 142) extending over an entire length of the sleeve (11) and in a cross section has a shape of a head (14'; 143, 148) with a connection neck (14"; 144, 147), so that the connection neck forms a retention undercut (14'''; 145, 146) on both sides, and the connection neck of the at least one retention element integrally formed offset to the apex line in a direction away from a pallatinal side and toward a buccal side of the sleeve, wherein a first retention undercut on the buccal side is smaller than a second retention undercut on the pallatinal side.

2. A bar matrix according to claim 1, wherein the at least one retention element (14; 142) has a buccal or lingual inclination, deviating from the occlusal direction.

3. A bar matrix according to claim 2, wherein an inclination of the at least one retention element (14; 142), as a deviation from the occlusal direction, is between 0° and 45°.

4. A bar matrix according to claim 2, wherein an inclination of the at least one retention element (14; 142), as a deviation from the occlusal direction, is between 10° and 30°.

5. A bar matrix according to claim 1, further comprising two parallel retention elements (141, 142) extending over the entire length of the sleeve (11), which both essentially have an occlusal alignment and enclose an angle ($\alpha$) amongst one another.

6. A bar matrix according to claim 5, wherein the angle ($\alpha$) which the two retention elements (141, 142) enclose with respect to one another, is maximally 90°, and the angle ($\alpha$) is preferably between 10° and 45°.

7. A bar matrix according to claim 5, wherein both of the retention elements (141, 142) in the cross section have the shape of the head (143, 148) with a connection neck (144, 147).

8. A bar matrix according to claim 7, wherein a length of the connection necks (144, 147) is different.

9. A bar matrix according to claim 1, wherein the head of the bar element has a flattening extending over the entire length.

10. A bar matrix according to claim 9, wherein the flattening runs perpendicular to an occlusal direction.

11. A bar matrix (10) according to claim 10, wherein the at least one retention element (14; 141, 142) extends over the entire length of the sleeve (11), and at one or more locations has undercut edges (16) transversely to a longitudinal direction of the retention element.

12. A bar matrix (10) according to claim 1, wherein the at least one retention element (14; 141, 142) extends over the entire length of the sleeve (11), and at one or more locations has undercut edges (16) transversely to a longitudinal direction of the retention element.

* * * * *